United States Patent [19]

Witt et al.

[11] Patent Number: 5,071,104

[45] Date of Patent: Dec. 10, 1991

[54] THREE-WAY ELASTIC VALVE FOR A WOUND IRRIGATION APPARATUS

[75] Inventors: Hillard T. Witt, Penn Valley; Allen W. Byers, Biggs, both of Calif.

[73] Assignee: Andermac, Inc., Yuba City, Calif.

[21] Appl. No.: 684,456

[22] Filed: Apr. 11, 1991

Related U.S. Application Data

[63] Continuation of Ser. No. 353,136, May 16, 1989, abandoned.

[51] Int. Cl.$^5$ ............................................. F16K 31/00
[52] U.S. Cl. .................................. 251/342; 604/142; 604/256
[58] Field of Search ................... 604/9, 169, 183, 185, 604/250-251, 255-256, 131, 140-142; 137/844; 251/342

[56] References Cited

U.S. PATENT DOCUMENTS

| | | | |
|---|---|---|---|
| 274,447 | 3/1883 | Kennish | 251/342 |
| 820,987 | 5/1906 | Perotti | 222/490 |
| 2,755,060 | 7/1956 | Twyman | 251/342 |
| 4,214,583 | 7/1980 | Arfaa | 604/142 |
| 4,267,835 | 5/1981 | Barger et al. | 251/342 X |
| 4,270,533 | 6/1981 | Andreas | 604/142 |
| 4,626,243 | 12/1986 | Singh et al. | 604/141 |

OTHER PUBLICATIONS

Pamphlet by Andermac, Inc., "Personal Care Products".

Leaflet by Andermac, Inc., "Hygenique Oral Irrigator".

Primary Examiner—C. Fred Rosenbaum
Assistant Examiner—Corrine Maglione
Attorney, Agent, or Firm—Townsend and Townsend

[57] ABSTRACT

A wound irrigation apparatus and process for safe cleansing of body wounds includes a pressure bladder disposed proximate a membrane sac holding a cleaning solution. Pressurizing the pressure bladder controllably pressurizes the cleaning solution. A conduit communicates the pressurized cleaning solution to a three-way valve. Operation of the normally off valve allows a steady stream of cleaning solution at a pressure of less than one atmosphere to be selectively directed to a wound for cleaning. The three-way valve includes an intermediate position which directs a gently pulsating stream of cleaning solution to the wound for enhanced cleaning action. The pulsation rate is directly dependent upon the pressure of the fluid and may be controlled. The valve includes a first elastic part and a second elastic part. The first part has an inlet with a larger diameter chamber into which the second part extends to form an integral valve unit. The second part includes a closed base within the chamber having a closed slit which is operable upon application of a compression force. The compression force resiliently collapses the closedbase end opening an orifice. Fluid flows through the orifice from the chamber out an outlet of the second part. Application of an intermediate compression force imparts a pulsation to the fluid stream emerging from the outlet.

1 Claim, 2 Drawing Sheets

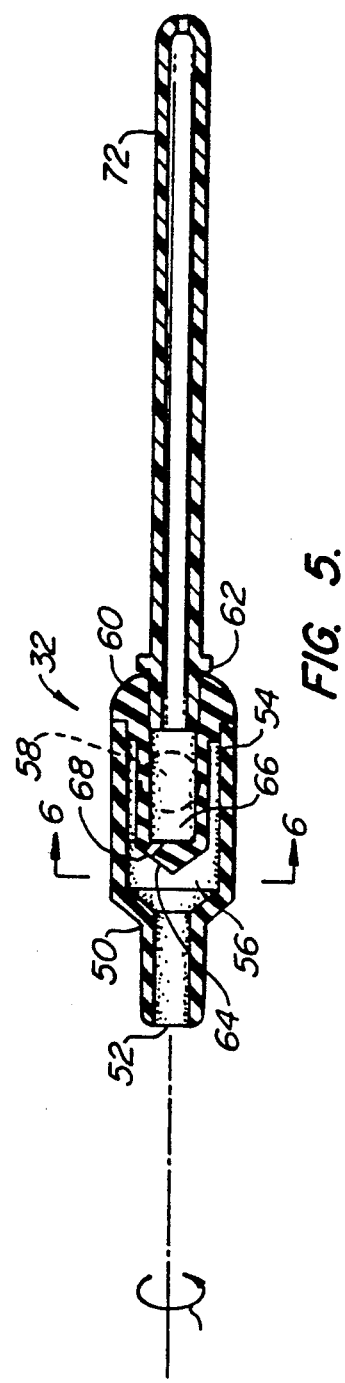
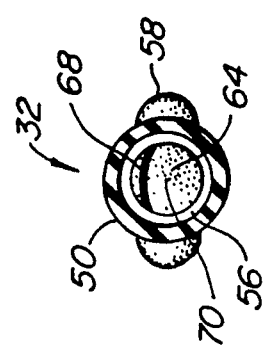
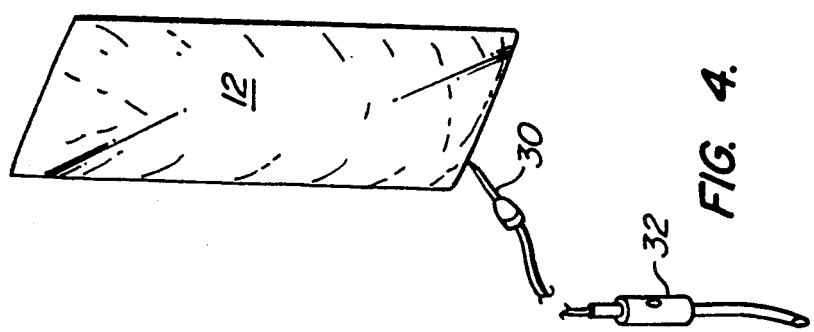

THREE-WAY ELASTIC VALVE FOR A WOUND IRRIGATION APPARATUS

This is a continuation of application Ser. No. 07/353,136, filed May 16, 1989, now abandoned.

BACKGROUND OF THE INVENTION

This invention relates generally to an apparatus for the treatment of disease infected body skin surface areas, such as in the mouth and gums. More particularly, the invention relates to an apparatus for the personalized and confidential administration of a sterile fluid by a person having a skin disorder requiring treatment outside of a hospital. The fluid is contained within a pressure vessel wherein it is manually and controllably pressurized and is then directed by means of a three position valve to a particular skin area to be treated. The valve provides for off, on, and intermittent operation.

SUMMARY OF THE PRIOR ART

The irrigation of wounds is a delicate and sensitive matter. Patients undergoing various medical procedures often acquire skin sores or lesions which require treatment. One instance of this would be the condition known as mucositis developed in cancer patients undergoing radiation or chemotherapy. Mucositis occurs in the mouth and effects the gums particularly. The gums need to be irrigated and cleansed. The particular fluid to effectively treat mucositis is variable and may be either tap water, sterile solutions, saline solutions, or other fluid. The treatment of the wound may be performed in a hospital ward, or it may be necessary to have a patient's wounds treated while the patient is away from the hospital's facilities. It is preferred that an irrigation system be operable by an individual patient in that the patient knows the best time a particular area requires attention. Likewise, certain wounds and their treatment may be a very private matter wherein the patient does not desire others to participate. An individualized and simple system will therefore permit more regular and thorough wound treatment if it may be performed by the patient in private.

An additional problem is that irrigation of a wound requires a low pressure stream to bathe the wound without exacerbating the condition. A delivery pressure of less than 12 psi ("pounds per square inch") is needed to prevent further traumatization and bruising of a wound. Again, a system should allow an individual patient to control the precise delivery pressure as the patient is best able to judge the effect the fluid stream has upon the wound.

A fluid delivery system must therefore be able to dispense any number of fluids as a directed and localized stream to any part of the body under the direction of a patient. The fluid stream must be portable, simple to operate, inexpensive and allow the pressure to be controlled and limited to less than 12 psi.

A device which couples to an ordinary faucet and dispenses ordinary tap water by use of an on-off valve is known in the art. Such a device is very practical for the post-surgical treatment of wounds of the peri-anal area, that is the vagina and the rectum, or as a douche in a hospital. Such a device has a coupling device to connect a tube from a faucet to an on and off valve. The valve would dispense fluid at whatever pressure was present at the faucet valve, limited by a pressure relief valve ("PRV") to reduce over pressure conditions. To adjust the pressure, the faucet controls would be operated. Such a device operates satisfactorily for its intended purposes, as a peri-anal irrigator or douche when fine controls over a reduced pressure are not as critical. Such a device may deliver too much pressure and has the added disadvantage that it must be operated near a faucet and may only dispense tap water. The reader will of course appreciate that this device is ineffectual to dispense sterile or antiseptic solutions.

It has been contemplated that commercially available dental devices which issue tap water for care of the teeth, such as a Water Pik TM, a registered trademark of Teledyne Industries, Inc., be used for oral irrigators or to treat wounds. These devices issue a fluid stream at approximately 50 psi which risks injuring the wound further. Also infirmities exist in that only tap water may be used, and it must be operated near either a faucet or an electrical outlet, or both.

The prior art has known low pressure fluid dispensers, usually in the form of syringes which receive a limited volume of liquid by drawing a piston back. The fluid contained in the syringe is dispensed by returning the piston to its first position, thereby discharging the fluid. This procedure is inconvenient and awkward to irrigate most wounds. The procedure of receiving and dispensing fluid must be repeated many times to properly irrigate a wound. As is understood, some patients may be incapable of operating this type of apparatus to properly irrigate their wounds.

SUMMARY OF THE INVENTION

An embodiment of the present invention effectively dispenses a sterile fluid from a manually pressurized pressure vessel for the confidential and select treatment of disease infected body skin surface areas. In the preferred embodiment, two bladders are provided, separated from one another by a membrane. A first bladder receives air from a manually operated pressure infuser. Pressure infusers are well known and operate to impart an increased air pressure to the first bladder, and permit control over the pressure imparted.

The second bladder contains the fluid to be dispensed. The fluid may be tap water, a home-made saline solution, a pre-made sterile solution, or some other fluid. The fluid in the second bladder is pressurized by virtue of the increased pressure in the first bladder and the proximity and structural relationship of the second bladder to the first.

A control valve is provided for coupling the pressurized fluid to an applicator tip. The control valve has three positions. There is a fully off, a fully on, and an intermittent position. The intermittent position provides a dispensing stream which pulsates. The pulsating stream has been discovered to provide a more positive cleansing action in that there is a tendency to "kick" debris out of a wound.

A novel valve is provided which is simple and inexpensive. Two elastic cylindrical pieces are coupled to one another and operate in a novel way. The first cylindrical piece has two open ends, a first end is provided with a fluid inlet. The second end is adapted to receive the second cylindrical piece. The second piece has a fluid outlet end and a second end adapted to be inserted inside the first piece. The second end of the second piece is closed except for an eccentrically located 45 degree angle slit across the base. Operation of the valve is performed simply by squeezing the first piece which has the second piece inserted inside. This constricting force causes the slit in the base of the second piece to open and permit pressurized fluid entering the fluid inlet to issue from the fluid outlet. If no constricting force is applied, the slit is closed, the valve is closed, and no fluid issues. If sufficient constricting force is applied to open the slit fully, the valve is fully open, and a steady stream issues from the fluid outlet. Intermittent to fully off and fully on, the valve operates in a pulsation mode. A constricting force somewhat less than that to obtain fully open operation results in the valve operating in the pulsation mode.

OTHER OBJECTS AND ADVANTAGES

An object of this invention is to provide for an apparatus to enable a patient to conveniently and effectively treat disease infected body skin surface areas while in the privacy of the home. The apparatus has a fluid chamber and means for manually pressurizing fluid within the chamber. A control valve is provided for the dispensing of the fluid. It is thus an object of the invention to allow a patient or operator a certain flexibility as to the type of fluid which may be dispensed and the location where a device embodying the invention may be used.

Thus, it is an advantage of the present invention which provides a patient with the potential to dispense tap water, home-made solutions, or pre-made solutions which may be sterile. Such a device permits portability in that it may be used outside a hospital's facilities. It is also portable in that the device may be used remote from faucets and power outlets.

The device has the added advantage that it is convenient in that it may be operated by the patients themselves.

Another advantage of this apparatus is that it is inexpensive, and personalized in that it permits a patient to privately self treat a wound, often without requiring additional assistance.

Another object is to provide for a controlled fluid stream having a pressure less than 12 psi. The pressure may be continuously controlled by a manually operated pressure infuser.

The advantage obtained by reduced pressure is the treatment of wounds without further injuring the patient. A reduced pressure stream will treat a wound and not bruise it or otherwise cause traumatization.

Another advantage of controlling the pressurization is that the sensitivity of patients and particular wounds is varied, and allowing a patient to individually set a particular pressure level will maximize cleansing action while minimizing pain and irritation.

Yet another advantage resulting from the control of pressure, is that it has been discovered that there is a direct relationship between pressure and the rate of pulsation while the valve is operated in the pulsation mode. Thus a patient wishing rapid pulsations could increase the pressure for particular treatments and could have a reduced pressure, with a slower pulsation rate, for other treatments.

A further object of the present invention is to provide an inexpensive and simple control valve which has three positions, an off, an on, and an intermittent position.

The intermittent position provides the advantage that a fluid stream which pulsates produces an effective cleaning action.

Yet another object of the invention is to provide for a sufficient volume of fluid to allow a patient to completely treat a wound without adding more fluid to a fluid container.

An advantage to such a device is that it makes wound treatment more convenient and efficient, contributing to a superior therapy program.

BRIEF DESCRIPTION OF THE DRAWINGS

Other objects, features, and advantages of this invention will be more apparent after referring to the specification and attached drawings in which:

FIG. 4 is a perspective view of a flexible membrane-walled fluid container containing a pre-made sterile solution which may be placed within a saddle of the present invention and a control valve with means for coupling to the solution as known in the art;

FIGS. 5 and 6 are detailed sectional views of the control valve of the present invention which has an off, an on, and an intermittent position, comprised of two elastic cylindrical pieces adapted to interface with one another, with one piece having a completely closed end except for an eccentrically located 45 degree angle slit as shown.

DETAILED DESCRIPTION OF A PREFERRED EMBODIMENT

Figure 1:
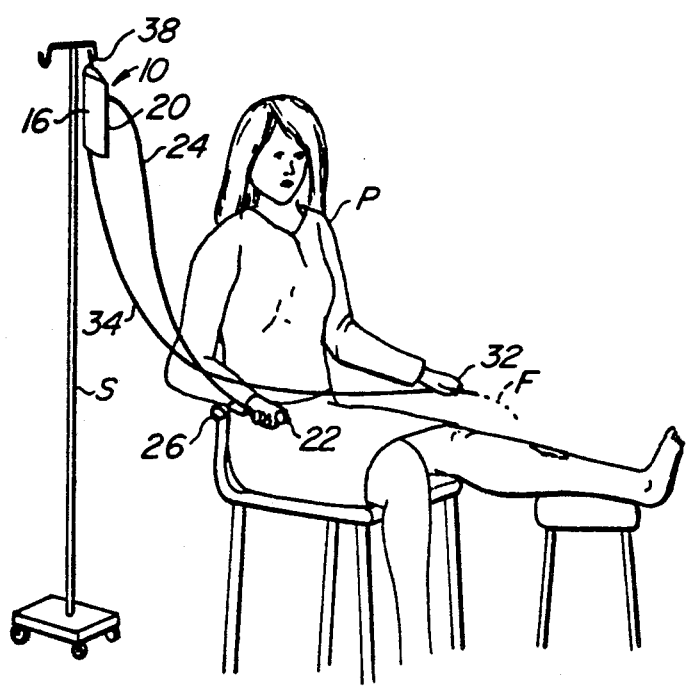
FIG. 1 is a perspective view showing a seated patient having a wound on one leg using an embodiment of this invention to treat the wound, wherein the patient operates an infuser with one hand, and directs a pulsating fluid stream onto the wound using the other hand.

FIG. 1 illustrates the utilization of an embodiment of the present invention to treat a disease infected skin surface area. A seated patient P having a skin disorder on a leg uses an irrigator 10 to dispense a fluid F onto the wound for its treatment. The irrigator 10 is shown suspended vertically from a stand S during operation by the patient P. The reader will understand that the device will operate in any orientation and without being suspended.

By references to FIGS. 2 and 3, preparation of the irrigator 10 for use will be described. Patient P (not shown) places a flexible walled membrane bladder 12, as shown in FIG. 4, containing a sterile pre-made solution of medicant into a saddle 16 formed on the back of an airtight pressure bladder 20. The saddle 16 serves as a restraining means to capture the flexible walled membrane bladder 12 next to the pressure bladder 20. Thus the reader will understand that there is at a minimum a single flexible wall between the pressure bladder 20 and the fluid within the membrane bladder 12. A pressure infuser 22 is provided for imparting an increased and controllable pressure to the pressure bladder 20. The pressure infuser 22 is in fluid communication via a polyvinylchloride ("PVC") tube 24 coupling the infuser 22 to a top portion of the pressure bladder 20. Means for governing the pressure imparted to the pressure bladder 20 are depicted as a pressure gauge 26. The reader will understand that other pressure controlling means, such as pressure relief valves ("PRV's"), may be employed in any part of the pressure system to control the pressure of the pressure bladder 20. Coupling means 30 is provided to enable a control valve 32 to be coupled in fluid communication with the medicant inside the membrane bladder 12 via a second pvc tube 34. The coupling means 30 is known in the art to permit a membrane bladder to be "spiked" and thereby access the sterile fluid inside the bladder. An example of membrane bladders and apparatus to administer the fluids are manufactured by Baxter-Travenol.

The coupling means 30 is attached at a bottom portion of the membrane bladder 12. Means for hanging the bag 38 are provided to permit the irrigator 10 to be mounted to the stand S as shown in FIG. 1. The hanging means 38 are known in the art for hanging plasma containing bags.

Figure 2:
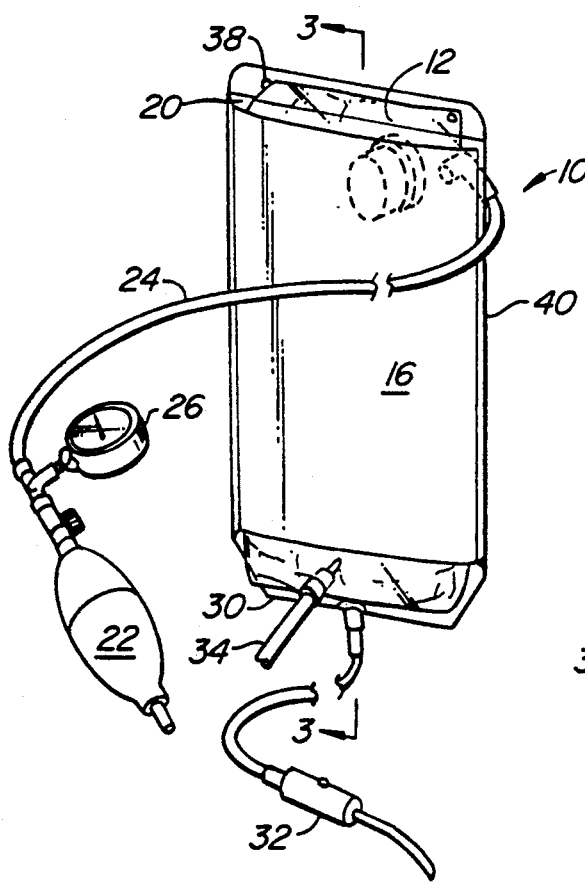
FIG. 2 is an illustration of a preferred embodiment showing a multifunctioned apparatus used to dispense a sterile solution from a membrane container, the apparatus has a bladder with a saddle holding the membrane container, a pressuring device communicated to the top of the bladder, and a control valve with applicator tip communicated to both the bottom of the bladder and the membrane container for possible simultaneous dispensing from the bladder and the container.
Figure 3:
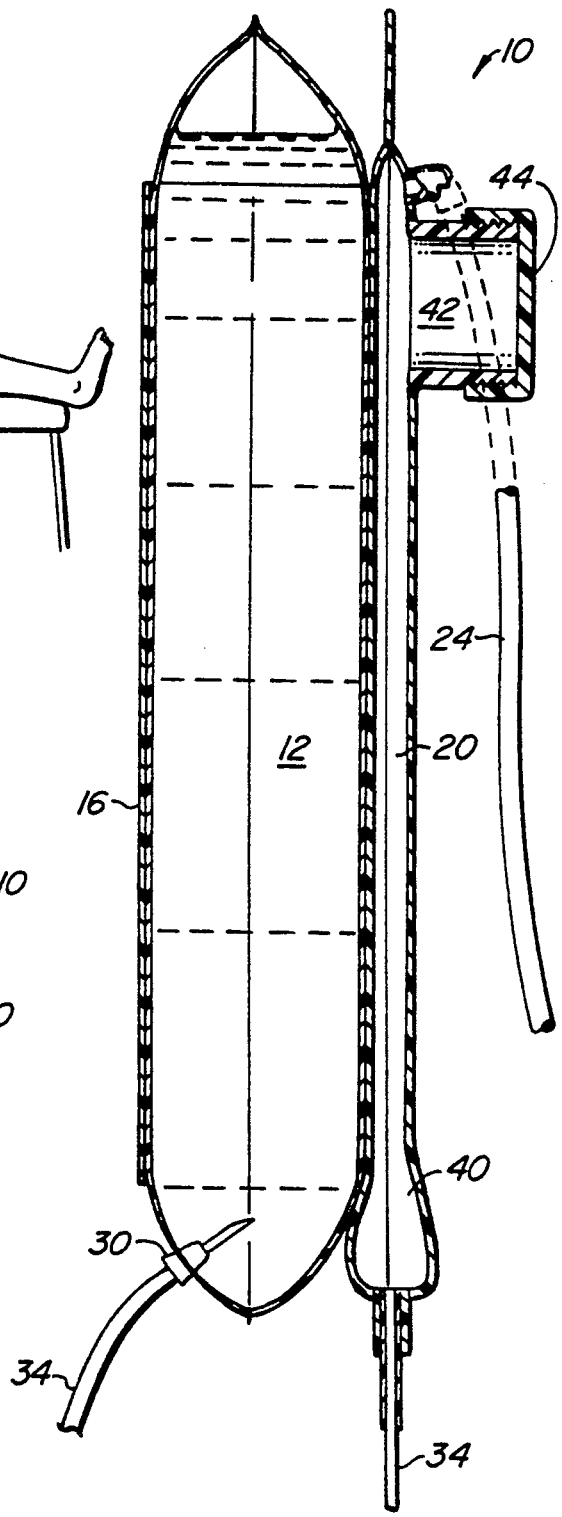
FIG. 3 is a detailed view taken as shown from FIG. 2 showing the interaction of the bladder and the membrane container, with the associated couplings.

Reference to FIGS. 2 and 3 indicate a second preferred embodiment of the wound irrigator 10. The irrigator 10 illustrated is useful when a fluid to be administered is not required to be sterile. Thus, the membrane bladder 12 and the pressure bladder 20 may be incorporated into a single pressurized fluid vessel 40. The fluid vessel 40 has connections virtually identical to the pressure bladder 20 shown in FIG. 1 except for the coupling of the control valve 32 (as shown in FIG. 2) via the tubing 34. In the fluid vessel 40, a homemade mix, or ordinary tap water, may be added through use of a filler tube 42. The fluid may be added to the vessel 40 and a filler cap 44 used to create both a water tight and an air tight seal. The reader will understand that fluid placed within the pressure vessel 40 will flow to the bottom portion of the vessel 40, as air will rise to the top portion of the vessel 40, when the vessel 40 is suspended vertically. The vertical suspension and relative separation of the fluid and air creates a fluid/air interface inside the vessel. The control valve 32 is coupled to the pressure vessel 40 along a bottom portion as is known in the art. The tubing 34 communicates the fluid in the vessel 40 to the control valve 32.

By reference to FIGS. 5-6, the construction of the control valve 32 may now be described. The control valve 32 comprises a first cylindrical part 50 having a fluid inlet end 52 and an outlet 54 in a fluid containing pressure chamber 56. The chamber 56 side walls are flexible and permit the pressure chamber 56 to be collapsed upon the application of an operating force. Diametrically opposed external protrusions 58 are provided at a point between the outlet 54 and the fluid inlet 52.

A second elastic part 60 is provided for mating to the first cylindrical part 50. The second part 60 has a fluid outlet end 62 and a sealed conical base end 64, wherein the second part 60 has an internal fluid channel 66 extending from the base end 64 to the fluid outlet end 62. Both the first part 50 and the second part 60 are made of an elastic material, such as rubber, which imparts a required flexibility and resiliency to the control valve 32 and its parts.

The base end 64 is sufficiently thick to permit compression loading by a compression force applied diametrically across the base end 64 whereby the base end 64 will collapse and fold upon itself upon application of the compression force and will return to its prestressed shape upon the removal of the compression force. The base end 64 has a slit 68 extending across a chord of a circle projected by an end view of the conical base end 64. The chord does not include the center of the projected circle, therefore it is eccentric about a longitudinal axis 70 of the second part 60. The slit 68 extends at a 45 degree angle to the longitudinal axis 70 through the base end 64. With the configuration just described, the reader should understand that a collapse and folding of the base end 64 with the slit 68 positioned as described caused by the compression force will cause an orifice to be formed in the base end 64.

The second part 60 is coupled to the first part 50 by inserting the base end 64 into the chamber 56 by passing through the outlet 54. The radial dimensions of the first part 50 and the second part 60 where the two mate is sufficient to provide an fluid tight seal between the periphery of the second part 60 and an internal surface of the outlet 54 of the first part 50. The positioning of the second part 60 in the first part 50 is important. The extension of the base end 64 into the chamber 56 should provide that the base end 64 is contained approximately in a plane containing the diametrically opposed protrusions 58. The preferred embodiment has the base end 64 extend past the plane containing the protrusions to a point close to where the fluid chamber 56 meets the fluid inlet 52. Additionally, the chord containing the slit should be substantially parallel to a line containing the protrusions 58.

It will be understood from the forgoing that without a compression force acting to fold the base end 64, the slit 68 does not form an orifice, thereby closing a fluid path from the fluid inlet 52 to the fluid chamber 56, through the slit 68 to the fluid channel 66, and then to the fluid outlet 62. A nozzle 72 may be attached to the fluid outlet 62 to facilitate the administration of fluid.

Next, the operation of an embodiment of the present invention will be explained by reference to FIGS. 1, 3, and 5.

A flexible walled membrane bladder 12, as shown in FIG. 4, containing a fluid F to be administered is selected. The membrane bladder 12 is placed within the saddle 16 of the irrigator 10. The coupling means 30 attached to the pvc tubing 34 is coupled to a bottom portion of the membrane bladder 12. Fluid F is communicated through the coupling means 30 and tubing 34 to the control valve 32. The fluid F enters the control valve 32 at the fluid inlet 52 and enters the fluid chamber 56. The fluid F surrounds the base end 64 and is prevented from entering the fluid channel 66 as there is no compression loading on the base end 64 to cause collapsing and folding whereby an orifice may be formed by said slit 68. The reader will therefore understand that the valve 32 is a normally closed valve, and no fluid F will be dispensed until the control valve 32 is operated.

Next, the pressure infuser 22 is pumped, as is well known in the art, to incrementally increase the pressure inside the pressure bladder 20. The pressure may be continuously monitored via the pressure gauge 26. The infuser is pumped until sufficient pressure is reached inside the pressure bladder 20. Satisfactory operation and treatment is obtained by maintaining the pressure below 12 psi, and superior operation is obtained by pressures in the 6-9 psi range.

As the pressure in the pressure bladder 20 is increased, pressure is imparted to the membrane bladder 12 due to the close proximity to the pressure bladder 20 and the restraining force exerted by the saddle 16. Thus, the reader will understand that the pressure imparted to the pressure bladder 20 directly imparts substantially the same pressure to the fluid F in the membrane bladder 12. By well known principles, the pressure imparted to the fluid F in the membrane bladder 12 is also the same pressure for the entire fluid path through the tubing 34 to the fluid chamber 56 in the control valve 32. Thus, the pressure measured by the pressure gauge 26 is substantially the pressure of the fluid F in the control valve. When the orifice is formed in the base end 64, the pressure of the fluid F will cause it to flow through the fluid path and be expelled at the same pressure.

To create the orifice, the control valve 32 is pinched at the protrusions, which applies an operating force to the control valve 32. The operating force collapses the flexible side walls of the first part 50 which permits the operating force to be applied to the base end 64 of the second part 60. By positioning the second part 60 in the first part 50 as described above, the operating force becomes the compression force which will collapse and fold the base end 64 to form the orifice. The positioning of the base end 64 ensures that the compression force is applied parallel to the chord containing the slit 68. This action of opening an orifice is similar to the operation of an elliptical rubberized coin purse which has a slit extending along a major axis of the purse. When the purse is squeezed along the major axis, the purse collapses and folds upon itself to produce an opening whereby articles may be placed in or removed from the purse. Essentially the same principle is applied here, wherein the squeezing of the protrusions 58 causes the base end 64 to be collapsed in the direction of the slit 68, causing it to open.

When sufficient operating force is applied to the control valve 32 to cause the base end 64 to completely collapse, the orifice completely opens to allow the pressurized fluid F in the chamber 56 virtually unrestricted access to the fluid channel 66 to be ultimately dispensed in a steady stream from the nozzle 72. By operating the valve in the on position, a substantially steady stream of fluid F under a controlled pressure may be directed at particular body skin surfaces which require treatment by the fluid F.

The control valve 32 also has an intermittent mode of operation as shown in FIG. 1 wherein the fluid F issuing from the nozzle 72 pulsates. The intermittent mode of operation is attained by applying an operating force intermediate to that force necessary to cause steady stream operation. The precise amount of force is dependent upon many factors including the stiffness of the materials and the dimensions of the valve. When the intermediate force is applied to the control valve 32, the base end 64 only partially collapses and folds to form a partially opened orifice. The partially opened orifice permits some of the pressurized fluid F in the fluid chamber 56 to exit through to the fluid channel 66 and thence to the nozzle 72. In flowing past the partially opened orifice, it is believed that the fluid F causes a bellowing effect inside the control valve 32 which causes an edge of the slit 68 to intermittently interfere with the fluid F stream to cause the fluid F issuing from the nozzle to pulsate. The pulsation imparted to the fluid flow is advantageous for the reasons cited above. The pulsation acts to "kick" debris out of a wound and provide an effective cleansing action. The intermittent mode may be interchanged with the on mode or the off mode, simply by controlling the amount of force squeezing the protrusions 58. By providing the three position valve, the appropriate cleaning action of the issuing fluid stream may be selected to provide a superior therapy program.

In the preferred embodiment of the control valve 32, as shown in FIGS. 5 and 6, the dimensions of the components comprising the control valve are as follows. The first part has an overall length of 1.2"-1.5". The fluid inlet 52 has an opening of 0.156" with a wall thickness of 0.05". The outlet 54 has an inside radius of 0.385", with a fluid chamber 56 length of 0.7"-1.0", with the protrusions located 0.5" from the back of the chamber opposite the outlet 54. The side wall thickness of the chamber 56 is 0.06". The second part 60 has a base end 64 having a conical section of 0.28" radius, and "height" 0.09". The length of the second part 60 extending into the fluid chamber 56 is 0.61". The fluid outlet 62 has a radius of 0.19". All dimensions are approximate and have tolerances of ±0.005". The nozzle 72 is approximately 3" long, 0.25" of which extend into the fluid outlet 62, with an exit aperture of the nozzle 72 of 0.06".

Applicant is aware that if the control valve 32 is constructed and operated as described, the resulting valve will function as explained. The applicant has discovered that the pulsation rate is directly related to the pressure of the fluid to be administered. As the pressure is increased, the rate at which the pulsations occur is increased. Additionally, applicants have discovered that shortening the fluid chamber 56 portion ahead of the protrusions so that the base end 64 extends past the plane containing the protrusions improves the pulsation rate of the stream issuing from the control valve 32. The shortened chamber 56 length is the preferred embodiment, as indicated above.

The reader will of course understand that an embodiment of this invention is not required to have a three position control valve 32 as described. The invention contemplates the operation with a simple on and off control to control the fluid stream.

The reader will understand that the operation of the device illustrated in FIG. 2 is substantially similar to the operation explained above. The devices differ in that in the irrigator 10 illustrated in FIG. 2, the incrementally increased pressure imparted to the pressure vessel 40 directly affects the fluid F also contained within the pressure vessel 40 at the fluid/air interface. Otherwise, the pressurized fluid F is communicated out of the pressure vessel 40 in response to an increased pressure in the vessel 40 infused by the pressure infuser 22. The fluid F is communicated to the control valve 32 via the pvc tubing 34 wherein the operation of the control valve 32 is the same as described above.

In summary, the irrigator 10 outlined above provides an economical, convenient, efficient, and confidential device to permit a patient P to treat disease infected body skin surfaces with a choice of solutions. The solutions may be pre-made sterile or antiseptic mixtures, or may be home-made or even ordinary tap water. The solution may be administered in the security of the patient's home, without significant effort or preparation. The pressure of the administered solution may be closely monitored and increased or decreased at the patients desire. The three position control valve provides ease of operation and improved treatment.

While the above provides a full and complete disclosure of the preferred embodiments of the present invention, various modifications, alternate constructions, and equivalents will occur to those skilled in the art given the benefit of this disclosure. Thus, the invention is not limited to the specific embodiment described herein, but is defined by the appended claims.

What is claimed is:

1. A manually operable digitally compressible elastic valve for dispensing pressurized liquid from a source of pressurized liquid at an inlet of said valve to a nozzle connected to an outlet of said valve responsive to manual compression across the valve body for:

(a) remaining in an off mode where no compressive force is applied across said valve body, (b) remaining open in an on mode where a constant opening compressive force is applied across said valve body, and (c) rapidly opening and closing in an intermittent flow mode where a constant force less than said constant opening force is applied across said valve body, said valve comprising:

a first elastic valve body part defining said valve inlet and extending into a first defined fluid containing pressure chamber, said first elastic valve body part defining on the exterior thereof opposed pressure points for collapsing said first defined fluid containing pressure chamber;

a second elastic valve body part, said second elastic valve body part having an open fluid outlet end communicated to said nozzle and a closed base end opposite to said open fluid outlet end, said closed base end defining a second fluid containing chamber having collapsible walls for collapse responsive to compression;

a slit disposed in said second elastic valve body part at said closed base end for remaining closed responsive to no force at said closed base end and opening the fluid chamber of said closed base end responsive to force across said closed base end of said second elastic valve body part, said slit at one end of said second elastic valve body part displaced by a spatial interval from said closed base end;

means mounting said second elastic valve body part with said closed base end extending into said first elastic valve body part at said first defined pressure chamber to dispose the collapsible walls of said closed base end of said second fluid containing chamber interior of the collapsible walls of said first defined pressure containing fluid chamber with said pressurized fluid therebetween;

said first collapsible valve body part at said first defined fluid containing pressure chamber capable of partial collapse at said opposed pressure points without compressing the collapsible walls of said closed end of said second elastic valve body part;

said closed end of said second elastic valve body part disposed to collapse said second elastic valve body part from said pressure points on said first valve body part at a location remote from said slit to open at said slit responsive to opening force from said pressure points on said first valve body part to collapse said first defined pressure chamber for compression of the walls of said second elastic valve body part around said closed chamber and to propagate from collapse of said walls of said second valve body part opening of said slit without direct compression of said second valve body part at said slit to open said slit to said on mode;

said closed end of said second elastic valve body part operable to intermittently open and close at said slit responsive to a less than opening force on said first valve body part from said pressure points on said first valve body part to collapse said first defined pressure chamber onto the closed base end of said second elastic valve body part for compression of the walls of said second elastic valve body part at said closed chamber to cause said valve to rapidly open and close in said intermittent mode.

* * * * *